(12) United States Patent
Wang et al.

(10) Patent No.: US 7,227,637 B2
(45) Date of Patent: Jun. 5, 2007

(54) MEASUREMENT SYSTEM WITH SEPARATE OPTIMIZED BEAM PATHS

(75) Inventors: David Y. Wang, Fremont, CA (US); Lawrence Rotter, Pleasanton, CA (US); Jeffrey T. Fanton, Los Altos, CA (US); Jeffrey E. McAninch, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 11/399,841

(22) Filed: Apr. 7, 2006

(65) Prior Publication Data

US 2006/0180761 A1    Aug. 17, 2006

Related U.S. Application Data

(63) Continuation of application No. 10/141,267, filed on May 8, 2002, now Pat. No. 7,061,614.

(60) Provisional application No. 60/329,819, filed on Oct. 16, 2001.

(51) Int. Cl.
*G01J 3/28* (2006.01)
*G01N 21/55* (2006.01)

(52) U.S. Cl. .................. 356/326; 356/445; 356/73

(58) Field of Classification Search ............... 356/326, 356/445, 73
See application file for complete search history.

(56) References Cited

U.S. PATENT DOCUMENTS

| | | | |
|---|---|---|---|
| 4,253,765 A | 3/1981 | Kato et al. ............... 356/328 |
| 4,322,165 A | 3/1982 | Ellebracht et al. ........ 356/316 |
| 4,672,196 A | 6/1987 | Canino ...................... 250/225 |
| 4,844,617 A | 7/1989 | Kelderman et al. ........ 356/372 |
| 5,166,752 A | 11/1992 | Spanier et al. ............. 356/369 |
| 5,373,359 A | 12/1994 | Woollam et al. ........... 356/328 |
| 5,486,701 A | 1/1996 | Norton et al. .............. 250/372 |
| 5,582,646 A | 12/1996 | Woollam et al. ........... 118/708 |
| 5,596,411 A | 1/1997 | Fanton et al. .............. 356/369 |
| 5,608,526 A | 3/1997 | Piwonka-Corle et al. ... 356/369 |
| 5,657,126 A | 8/1997 | Ducharme et al. ......... 356/369 |

(Continued)

FOREIGN PATENT DOCUMENTS

DE    201 08 171 U1    5/2001

OTHER PUBLICATIONS

R.L. Johnson et al., "Design and Performance of a VUV Ellipsometer," *Nuclear Instruments and Methods in Physics Research*, vol. A290, 1990, pp. 606-612.

(Continued)

*Primary Examiner*—Layla G. Lauchman
*Assistant Examiner*—Kara Geisel
(74) *Attorney, Agent, or Firm*—Stallman & Pollock LLP

(57) ABSTRACT

The subject invention relates to a broadband optical metrology system that segregates the broadband radiation into multiple sub-bands to improve overall performance. Each sub-band includes only a fraction of the original bandwidth. The optical path—the light path that connects the illuminator, the sample and the detector—of each sub-band includes a unique sub-band optical system designed to optimize the performance over the spectral range spanned by the sub-band radiation. All of the sub-band optical systems are arranged to provide small-spot illumination at the same measurement position. Optional purging of the individual sub-band optical paths further improves performance.

21 Claims, 3 Drawing Sheets

U.S. PATENT DOCUMENTS

| | | | |
|---|---|---|---|
| 5,805,285 A | 9/1998 | Johs et al. | 356/369 |
| 5,872,630 A | 2/1999 | Johs et al. | 356/369 |
| 6,151,116 A | 11/2000 | Hirosawa | 356/369 |
| 6,184,985 B1 | 2/2001 | Chalmers et al. | 356/381 |
| 6,222,199 B1 | 4/2001 | Freeouf | 250/559.27 |
| 6,256,097 B1 | 7/2001 | Wagner | 356/369 |
| 6,268,917 B1 | 7/2001 | Johs | 356/369 |
| 6,278,519 B1 | 8/2001 | Rosencwaig et al. | 356/369 |
| 6,307,627 B1 | 10/2001 | Vurens | 356/369 |
| 6,426,502 B1 | 7/2002 | Finarov | 250/348 |
| 6,535,286 B1 | 3/2003 | Green et al. | 356/369 |
| 6,628,397 B1 | 9/2003 | Nikoonahad et al. | 356/445 |
| 6,813,026 B2 | 11/2004 | McAninch | 356/445 |
| 2002/0126283 A1 | 9/2002 | Drevilion et al. | 356/369 |
| 2002/0149774 A1* | 10/2002 | McAninch | 356/445 |
| 2003/0160877 A1* | 8/2003 | Sumida | 348/188 |
| 2004/0150820 A1 | 8/2004 | Nikoonahad et al. | 356/364 |

OTHER PUBLICATIONS

M. Kildemo et al., "Real time monitoring of the growth of transparent thin films by spectroscopic ellipsometry," *Rev. Sci. Instrum.*, vol. 67, No. 5, May 1996, pp. 1956-1960.

R.L. Johnson et al., "Spectroscopic ellipsometry with synchrotron radiation," *Rev. Sci. Instrum*, vol. 60, No. 7, Jul. 1989, pp. 2209-2212.

T. Saito et al., "Application of oblique incidence detector to vacuum ultraviolet polarization analyzer," *Rev. Sci. Insturm.*, vol. 66, No. 2, Feb. 1995, pp. 1570-1572.

P. Boher et al., presentation of Sopra, entitled "Characterisation of thin films and multilayers in the VUV wavelength range using spectroscopic ellipsometry and spectroscopic photometry," May 8-90, 2000, pp. 759-786.

P. Boher et al., "A New Purged UV Spectroscopic Ellipsometer to characterize thin films and multilayers at 157nm," *SPIE*, vol. 3998 (2000), pp. 379-389.

J.N. Hilfiker et al., "Optical characterization in the vacuum ultraviolet with Variable Angle Spectroscopic Ellipsometry: 157 nm and below," *SPIE*, vol. 2998 (2000), pp. 390-398.

* cited by examiner

10

40

50

MEASUREMENT SYSTEM WITH SEPARATE OPTIMIZED BEAM PATHS

PRIORITY CLAIM

This application is a continuation of application Ser. No. 10/141,267, filed May 8, 2002 now U.S. Pat. No. 7,061,614, and claims priority to U.S. Provisional Patent Application Ser. No. 60/329,819, filed Oct. 16, 2001, which are incorporated herein by reference.

TECHNICAL FIELD

The subject invention relates to the field of optical metrology, particularly broadband optical metrology tools that may require a controlled ambient to eliminate the effects of atmospheric optical absorption. Specifically, the invention relates to an optical metrology instrument that includes optimized, spectrally segregated optical systems and gas purged optical paths to improve system performance.

BACKGROUND OF THE INVENTION

In the prior art there has been considerable effort expended in extending the spectral bandwidth, or wavelength range, of a broad class of optical metrology instruments. Non-contact, optical measurements are heavily utilized in the optics, optical communications and semiconductor industries. The instruments are used in the evaluation and characterization of samples that can include spatially non-uniform distributions of a broad class of materials including, insulators, semiconductors and metals; consequently, the optical properties of these samples can vary markedly with wavelength. Hence, in general, a much greater wealth of information can be extracted from broadband spectroscopic measurements than can be obtained from measurements made over a narrow spectral range. One approach to implementing broadband spectroscopic measurements is set forth in U.S. Pat. No. 6,278,519, which is incorporated herein by reference.

At present, leading-edge industrial lithography systems operate in the DUV over a narrow wavelength region of approximately 193 nm. State-of-the art optical metrology systems that operate over the spectral range spanning the DUV-NIR (190 nm-850 nm) characteristically employ two lamps to span this range of measurement wavelengths, a Deuterium lamp for spectroscopic measurements between 190 and 400 nm, and a Xenon lamp for measurements between 400 nm and 800 nm.

In the near future systems will operate in the vacuum ultra-violet at an exposure wavelength of 157 nm. Wavelengths in the range between 140 nm-165 nm lie within a region known as the vacuum ultraviolet (VUV), in which the high absorption coefficients of oxygen and water vapor lower the attenuation length in standard air to fractions of a millimeter. (Historically, this light could only be observed under vacuum conditions, hence the designation.) Achieving the transmission and stability necessary for optical metrology in the VUV, in a tool where the optical paths are of order 0.5-2 m requires oxygen and water concentrations in the low parts-per-million (ppm) range averaged over the entire optical path. One approach to achieving this is described in copending U.S. application Ser. No. 10/027385, filed Dec. 21, 2001, now U.S. Pat. No. 6,813,026, and incorporated herein by reference, which discloses a method for inert gas purging the optical path.

The technology extension requires that the measurement bandwidth of optical metrology tools be broadened to cover the wavelength range spanning 140-850 nm. This is a daunting challenge.

First, optical systems that spectrally segregate the illumination with diffractive elements must account for and suppress unwanted signals produced by harmonic contamination. For example, at wavelength $\lambda$ a diffraction grating will produce a $1^{st}$ order an intensity maximum at an angular position $\theta$; at a wavelength $\lambda'=\lambda/2$ the same grating, in the $2^{nd}$ order, also produces an intensity maximum at $\theta$. Consequently, when 140 nm light impinges upon a diffractive grating in addition to the $1^{st}$ order diffracted beam, there are $2^{nd}$, $3^{rd}$, $4^{th}$, $5^{th}$ and $6^{th}$ etc. diffractive orders that appear at angular positions corresponding to $1^{st}$ order diffraction at 280 nm, 420 nm, 560 nm, 700 nm and 840 nm light, etc., respectively. Consequently spectrometers that use diffraction gratings to disperse the light must, at a minimum, include order-sorting, optical filters to suppress contributions from the higher orders.

Second, most common optical materials undergo solarization, structural and electronic changes to the material that occur upon exposure to VUV and DUV light. VUV and DUV exposure can significantly modify and degrade material optical properties. To avoid the adverse effect of solarization, refractive VUV optical systems must exclusively employ wide bandgap optical materials such as $CaF_2$, $MgF_2$, LiF, and LaF3.

Third, virtually all optical materials are dispersive; i.e. the material refractive index varies as a function of wavelength, or optical frequency. Therefore, the focal position of an individual lens will be wavelength dependent giving rise to chromatic aberration of the lens. This phenomenon complicates the design of broadband optical systems. Chromatic correction can be achieved, to a limited extent, using lenses with multiple optical elements fabricated from at least two optical materials. The general idea is to select and configure components so that there is partial cancellation of the chromatic effects, thereby increasing the useful wavelength range. The designs may be very complex and involve the use of multiple components arranged in multiple groups. The complexity of the optical design and the cost of system fabrication increase with the optical bandwidth.

Note that, to some extent, requirements two and three above are mutually exclusive. It may not be practical to provide a lens design that simultaneously exhibits good transmission in the VUV and chromatic correction over the 140 to 850 nm wavelength range. As proposed herein, one solution to this problem is to spectrally segregate the broadband light and provide multiple lens systems. Each lens operates over a limited wavelength range, or optical subband. The sum of the sub-bands constitutes the overall system bandwidth. Here, each lens is designed to operate over a limited wavelength range. This may permit a simpler optical design to be used in each of the sub-band lenses and provide a system architecture that provides superior broadband optical performance at reduced system cost.

Accordingly it would be desirable to provide a metrology tool architecture that permits extension of the measurement bandwidth over the spectral region spanning the VUV-NIR 140 nm-850 nm and avoids the problems associate with atmospheric absorption, chromatic aberration and harmonic contamination.

The acronyms used in this specification have the following meanings:
CD=critical dimension
DUV=deep ultraviolet VUV=vacuum ultraviolet
NIR=near infrared

SUMMARY OF THE INVENTION

The subject invention relates to a broadband optical metrology system that optimizes performance by dividing the broadband illumination into multiple sub-bands, such that each sub-band spans only a fraction of the frequency width of the original broadband spectrum. The sub-band illumination is transmitted along a unique sub-band optical path that connects the illuminator, the sample and the detector. The sub-band optical path includes a sub-band optical system that is optimized for the range of frequencies contained within the sub-band. In this fashion, a single broadband measurement constitutes multiple narrow-band measurements.

Ideally, the individual sub-band optical systems are arranged to produce small-spot illumination of the sample and are configured such that all systems illuminate the sample at the same location. In this way, the broadband information is derived from probing the same spatial region of the sample. The highest system throughput is achieved when the simultaneous measurements are made over all of the sub-bands. To circumvent the adverse effects of atmospheric optical absorption (particularly problematic in the VUV) the sub-band optical path can be purged with an optically transparent gas such as $N_2$ or He.

BRIEF DESCRIPTION OF THE DRAWINGS

FIG. 1 is a schematic diagram illustrating separate light paths between the source and sample.

FIG. 2 is a schematic diagram illustrating separate light paths between the sample and detector.

FIG. 3 is a schematic diagram illustrating separate paths between the source and the detector.

FIG. 4 is a schematic diagram illustrating a single broadband source and separate light paths between the sample and detector.

DETAILED DESCRIPTION OF THE PREFERRED EMBODIMENTS

FIGS. 1 through 6 are schematic and a highly simplified optical representation has been used to reduce the complexity of the drawings. Herein individual optical components are used to represent functional elements that may be quite complex; for example, a lens in these figures represents an optical system for collecting and focusing light—the physical embodiment of the optical system may employ multiple lenses in multiple groups.

Figure 1:
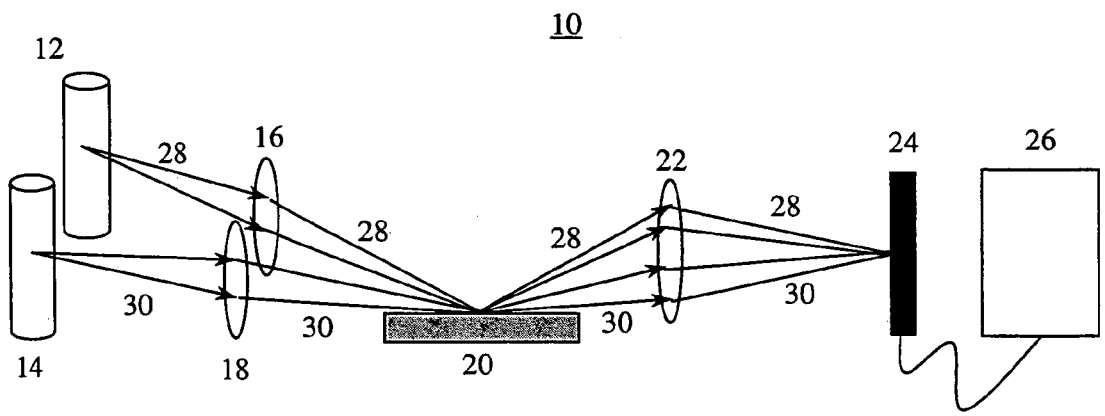
FIGS. 1 through 4 are schematic diagrams of a generalized optical metrology system comprising illuminator, sample, detector, processor with two light sources and two separate sub-band optical paths. Four representative arrangements of the sub-band optical systems are illustrated.

FIG. 1 illustrates an embodiment of the invention 10, wherein two spectrally segregated light sources 12 and 14 are used to illuminate the sample. Light source 12 emits illumination over a first spectrum. The optical path 28 traversed by light of the first spectrum includes light source 12, optical system 16, sample 20, optical system 22 and detector 24. Optical system 16 focuses a portion of the light emitted by source 12 onto sample 20 where the light interacts with and reflects from the sample. A portion of the reflected radiation is collected by optical system 22 and focused onto detector 24. Detector 24 generates output signals in response to the detected illumination and processor 26 records and analyzes those signals.

Light source 14 emits illumination over a second spectrum substantially different from the first. The optical path 30 traversed by light of the second spectrum includes light source 14, optical system 18, sample 20, optical system 22 and detector 24. Optical system 18 focuses a portion of the light emitted by source 14 onto sample 20 where the light interacts with and reflects from the sample. A portion of the reflected radiation is collected by optical system 22 and focused onto detector 24. Detector 24 generates output signals in response to the detected illumination and processor 26 records and analyzes those signals.

Note that in this arrangement the optical paths 28 and 30 in the region between sample 20 and detector 24 are substantially identical. However, those portions of optical paths 28 and 30 between source 12 and sample 20, and source 14 and sample 20 are different. The spatial separation of the light contained within the first and second spectra permits optical systems 16 and 22 to be designed to optimize performance over a limited spectral range: optical system 16 is optimized for wavelengths included within the first spectrum, optical system 18 is optimized for wavelengths included within the second spectrum.

Optical systems 16 and 18 are configured to illuminate the sample at the same location with substantially identical spot-sizes. In this way, the aberrations of both optical systems may be reduced which permits superior focusing performance and a smaller illuminated region on the sample, which, in turn, permits measurement of smaller regions of the sample and the measurement of smaller features.

The arrangement admits several variations. For example in one arrangement both light sources are broadband, e.g. light source 12 is a Xe lamp and light source 14 is a deuterium lamp. In this case optical system 16 is optimized for performance over a wavelength range spanning approximately 400-850 nm. Optical system 18 is optimized for performance over a wavelength range spanning approximately 190-400 nm.

Different optimization criteria may be employed in designing optical systems 16 and 18. For example, it may be important to insure that an identical illumination spot is used to probe the sample at all illumination wavelengths, i.e. the optical designs must minimize chromatic aberration. Generally, chromatic aberrations of optical systems increase with the range of operating wavelengths; therefore, chromatic correction is more readily accomplished over a limited wavelength range. Optical system 18 is designed to operate over a sub-band of optical frequencies spanning the wavelength range between 190 and 400 nm. Similarly, optical system 16 is designed to operate over a sub-band of optical frequencies spanning the wavelength range between 400 and 850 nm. Superior correction can be achieved over the entire range of operating wavelengths since optical systems 16 and 18 may be individually chromatically corrected over their respective sub-band frequencies.

In the present case the optimum design for optical systems 16 and 18 may be very different, with each system employing a unique set of optical elements fabricated from unique materials. For example, optical system 18 will require the use of higher quality and therefore more expensive UV compatible optical materials such as UV grade fused silica and $CaF_2$. Optical system 16 may employ a wider variety of lower cost optical materials.

Alternatively, cost may be the most important factor governing the optical design and a given degree of chromatic aberration may be acceptable. As discussed above, chromatic correction of two individual sub-band optical systems is simpler and requires fewer optical elements than chromatic correction of a single broadband optical system that spans the entire wavelength range. Since fewer elements are required the cost is reduced.

Additionally, it may be desirable to provide superior environmental control for one of the sub-band optical systems, e.g. sub-band optical system 18 which operates over the wavelength region spanning 190–400 nm. In this case, and as illustrated in the preferred embodiments of FIGS. 3–6, it is desirable to house the optical system in an enclosure purged with inert gas. Gas purging can prevent unwanted optical absorption and mitigate against degradation of the sub-band optics due to chemical adsorption of reactive species on the optical surfaces. The concept of optimizing a sub-band optical path can include selection or design of lenses and other optical elements and/or environmental controls which can improve the performance of the system.

Lastly, although the preceding discussion has been undertaken with regard to the use of broadband sources, one or both of light sources 12 and 14 may be a laser. In this case optical systems 16 and/or 18 are optimized at the laser wavelength(s).

The arrangement of FIG. 1 may be generalized to include multiple light sources and multiple optical systems. Furthermore, it may be employed in systems that include one or more optical systems used separately or in combination including reflectometers, ellipsometers, scatterometers, and optical CD metrology tools operating as single wavelength metrology systems and broadband spectroscopic instruments.

Figure 2:
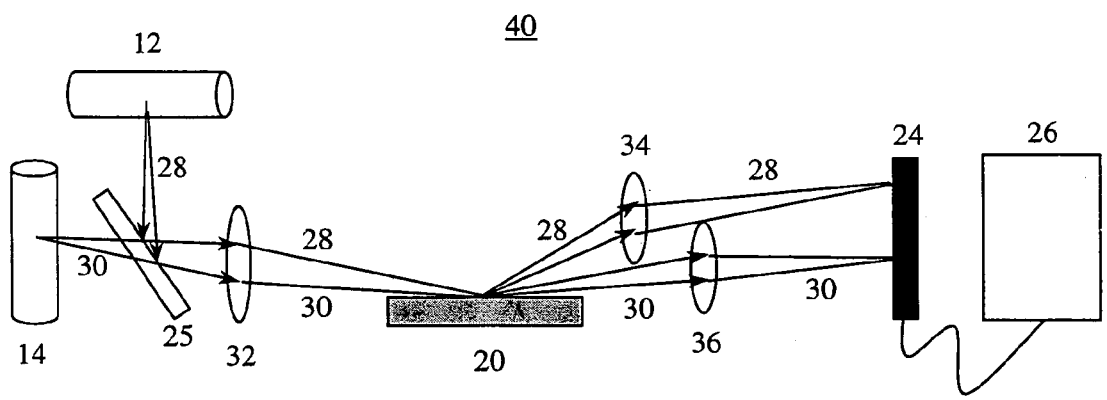

FIG. 2 illustrates an embodiment of the invention 40, wherein two spectrally segregated light sources 12 and 14 are used to illuminate the sample. Light source 12 emits illumination over a first spectrum and light source 14 emits illumination over a second spectrum. The optical path 28 traversed by light of the first spectrum includes light source 12, beam combiner 25, optical system 32, sample 20, optical system 34 and detector 24. The optical path 30 traversed by light of the second spectrum includes light source 14, beam combiner 25, optical system 32, sample 20, optical system 36 and detector 24.

Note that optical paths 28 and 30 are substantially coincident in the region between beam combiner 25 and sample 20 and that optical system 32 is used to provide small-spot illumination of sample 20 with light originating from both of the light sources 12 and 14. Beam combiner 25 may be a prism, a beam-splitter, a dichroic mirror, or other suitable element which functions to combine a portion of the light emitted by sources 12 and 14.

Following reflection from sample 20 light paths 28 and 30 diverge. A portion of the reflected illumination with wavelengths within the first spectrum is collected by optical system 34, and a portion of the reflected illumination with wavelengths within the second spectrum is collected by optical system 36. Optical systems 34 and 36 are separately optimized for the spectral regions spanning the first and second spectra respectively. In this way, the aberrations of both optical systems may be reduced which permits superior detection performance.

Optical systems 34 and 36 focus the collected ration onto detector 24. Detector 24 generates output signals in response to the detected illumination and processor 26 records and analyzes those signals.

The arrangement admits several variations. For example in one arrangement both light sources are broadband, e.g. light source 12 is a Xe lamp and light source 14 is a deuterium lamp. Here optical system 34 is optimized for performance over a wavelength range spanning approximately 400–850 nm. Optical system 36 is optimized for performance over a wavelength range spanning approximately 190–400 nm. In another arrangement one or both of the sources 12 and 14 may be a laser. In this case optical systems 34 and/or 36 are optimized at the laser wavelength(s).

The arrangement of FIG. 2 may be generalized to include multiple light sources and multiple optical systems. Furthermore, it may be employed in systems that include one or more optical systems used separately or in combination including reflectometers, ellipsometers, scatterometers, and optical CD metrology tools operating as single wavelength metrology systems and broadband spectroscopic instruments.

Figure 3:
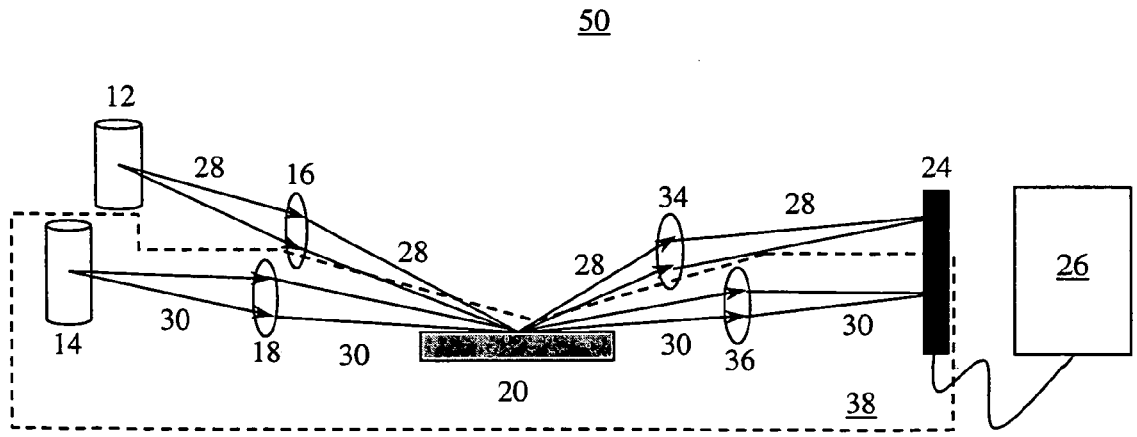

FIG. 3 illustrates an arrangement of the invention 50 that employs separate optical paths for each of the spectrally separated light sources 12 and 14. Light source 12 emits illumination over a first spectrum. The optical path 28 traversed by light of the first spectrum includes light source 12, optical system 16, sample 20, optical system 34 and detector 24. Optical system 16 focuses a portion of the light emitted by source 12 onto sample 20 where the light interacts with and reflects from the sample. A portion of the reflected radiation is collected by optical system 34 and focused onto detector 24. Detector 24 generates output signals in response to the detected illumination and processor 26 records and analyzes those signals.

Light source 14 emits illumination over a second spectrum substantially different from the first. The optical path 30 traversed by light of the second spectrum includes light source 14, optical system 18, sample 20, optical system 36 and detector 24. Optical system 18 focuses a portion of the light emitted by source 14 onto sample 20 where the light interacts with and reflects from the sample. A portion of the reflected radiation is collected by optical system 22 and focused onto detector 24. Detector 24 generates output signals in response to the detected illumination and processor 26 records and analyzes those signals.

The spatial separation of the light contained within the first and second spectra permits optical systems 16 and 22 to be designed to optimize performance over a limited spectral range: optical system 16 is optimized for wavelengths included within the first spectrum, optical system 18 is optimized for wavelengths included within the second spectrum. Optical systems 16 and 18 are configured to illuminate the sample at the same location with substantially identical spot-sizes.

In this way, the aberrations of both optical systems may be reduced which permits superior focusing performance and a smaller illuminated region on the sample, which, in turn, permits measurement of smaller regions of the sample and the measurement of smaller features. Further, optical systems 34 and 36 are separately optimized for the spectral regions spanning the first and second spectra respectively. In this way, the aberrations of both optical systems may be reduced which permits superior detection performance.

The arrangement admits several variations. For example in one arrangement both light sources are broadband, e.g. light source 12 is a Xe lamp and light source 14 is a deuterium lamp. Here optical systems 16 and 34 are optimized for performance over a wavelength range spanning approximately 400–850 nm. Optical systems 18 and 36 are optimized for performance over a wavelength range spanning approximately 190–400 nm. In another arrangement one or both of the sources 12 and 14 may be a laser. In this case optical systems 16 and/or 18 are optimized at the laser wavelength(s).

The arrangement of FIG. 3 may be generalized to include multiple light sources and multiple optical systems. Furthermore, it may be employed in systems that include one or more optical systems used separately or in combination including reflectometers, ellipsometers, scatterometers and optical CD metrology tools operating as single wavelength metrology systems and broadband spectroscopic instruments.

The separation of the light paths illustrated in FIG. 3 has further advantages. For example, one or more of the measurement systems may be maintained in a purged environment. In FIG. 3 the metrology system comprising source 14, light path 30, optical system 18, sample 20, optical system 36 and a portion of detector 24 is located within a purged region 38. In practice, region 38 may include several isolated regions and enclosures that surround the system components 14, 18, 36, and portions of 24, and beam transport tubes which surround the optical paths that connect the system components and the sample. Region 38 may be purged of atmospheric constituents using inert gas such as $N_2$ or He permitting improvement of the system performance and extension of the operating wavelengths into the VUV spectral region, including the 157 nm wavelength ($F_2$ laser transition) used in leading-edge optical lithography. (See the above cited copending U.S. application Ser. No. 10/027385, now U.S. Pat. No. 6,813,026, for discussions of purging technology.)

For VUV applications, optical systems 18 and 36 are optimized for performance over a spectral range spanning a portion of the spectral region between 140 and 190 nm and employ optical components made from VUV compatible materials selected from the group consisting of UV grade fused silica, $CaF_2$, $BaF_2$, $LaF_3$, LiF, $SrF_2$, $MgF_2$ and fluorine doped fused silica.

The arrangement admits several variations. For example in a preferred embodiment including two broadband light sources light source 12 is a Xe lamp and light source 14 is a deuterium lamp that includes a VUV window. A separate, gas purged metrology system is used for measurement over the spectral range spanning the spectral region between 140 and 190 nm. In the spectral region between 190 and 850 nm, the remainder of the system is configured as illustrated in FIG. 1, e.g. both sources illuminate the sample, and a common path optical system 22 and detector 24 are employed.

The arrangement of FIG. 3 may be further generalized to include multiple light sources, multiple optical systems and multiple purging systems. Furthermore, it may be employed in systems that include one or more optical instruments used separately or in combination including reflectometers, ellipsometers, scatterometers, and optical CD metrology tools operating as single wavelength metrology systems and broadband spectroscopic instruments.

Figure 4:
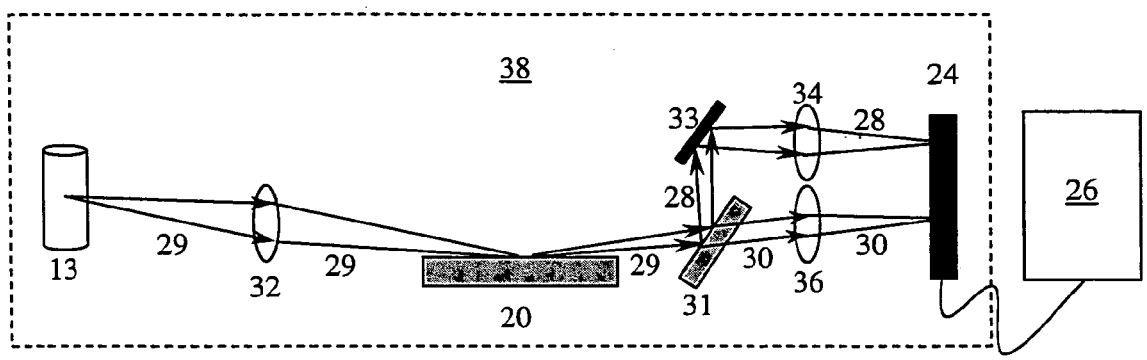

FIG. 4 illustrates an arrangement of the invention that employs a single ultra-broadband light source 13. By ultra-broadband we mean to indicate that the light source emits illumination over a very broad spectral range including, for example, the DUV and VUV, or the DUV, visible and NIR, or the VUV, DUV, visible, and NIR.

A portion of the illumination 29 emitted by ultra-broadband light source 13 is collected by broadband optical system 32 and focused to provide small-spot illumination of sample 20. The incident illumination interacts with and reflects from sample 20. A portion of the reflected illumination is incident onto beamsplitter 31 that divides the reflected portion into two spectrally segregated optical beams 28 and 30.

The spectral segregation may be accomplished with a one or more elements selected from the group consisting of, for example, dichroic mirrors, grating, prisms or their equivalent. Beam 28 comprises a first sub-band spectrum that includes illumination with wavelengths or frequencies spanning a first portion of the original ultra-broadband spectrum. Similarly, beam 30 comprises a second sub-band spectrum that includes illumination with wavelengths or frequencies spanning a second portion of the original ultra-broadband spectrum.

In the preferred embodiment illustrated in FIG. 4, beamsplitter 31 is a dichroic mirror, which is designed to reflect the first sub-band spectrum 28 and transmit the second sub-band spectrum 30. Illumination within the first sub-band spectrum reflects from fold-mirror 33 and is collected and focused by sub-band optical system 34 onto detector 24. Illumination within the second sub-band spectrum is transmitted through dichroic mirror 31, and collected and focused by sub-band optical system 36 onto detector 24. Detector 24 generates output signals in response to the detected illumination and processor 26 records and analyzes those signals.

The spectral segregation of the light contained within the first and second spectra permits optical systems 34 and 36 to be designed to optimize performance over a limited spectral range: optical system 34 is optimized for wavelengths included within the first spectrum, optical system 36 is optimized for wavelengths included within the second spectrum. In this way, the aberrations of both optical systems may be reduced which permits superior detection performance.

In this arrangement, the spectrally segregated light reaching detector 24 is also spatially separated. Consequently, as illustrated in FIG. 4, detector 24 could consist of two detectors: a first detector optimized for the wavelength region comprising the first sub-band spectrum and a second detector optimized for the wavelength region comprising the second sub-band spectrum.

Further, the metrology system comprising source 13, light path 29, optical system 32, sample 20, beamsplitter 31, light paths 28 and 30, fold mirror 33, optical systems 34 and 36 and a detector 24 may be located within a purged region 38. In practice, region 38 may include several isolated regions and enclosures that surround the system components 14, 18, 36, and portions of 24, and beam transport tubes which surround the optical paths that connect the system components and the sample. Region 38 may be purged of atmospheric constituents using inert gas such as $N_2$ or He permitting improvement of the system performance and extension of the operating wavelengths into the VUV spectral region.

The arrangement of FIG. 4 may be generalized to include multiple light sources and multiple optical systems. Furthermore, it may be employed in systems that include one or more optical systems used separately or in combination including reflectometers, ellipsometers, scatterometers and optical CD metrology tools operating as single wavelength metrology systems and broadband spectroscopic instruments.

Figure 5:
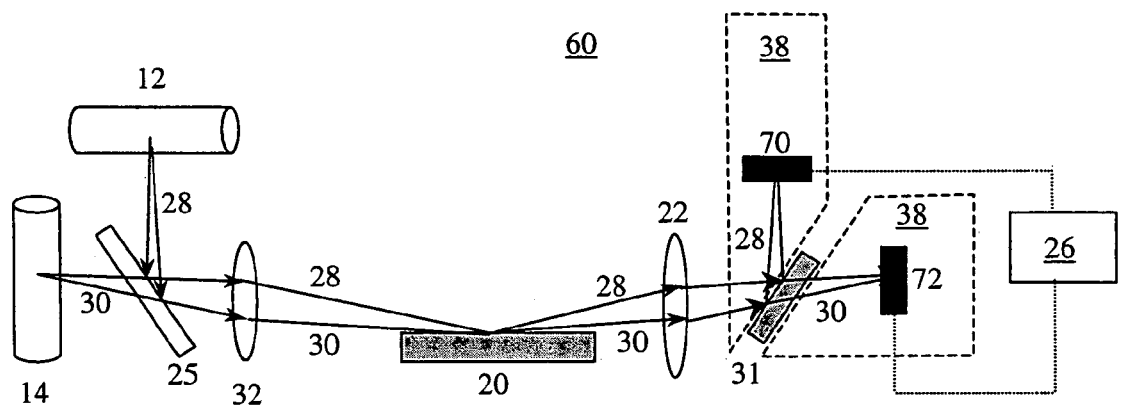
FIG. 5 is a schematic diagram illustrating common optical paths with separate detectors

FIG. 5 illustrates an embodiment of the invention 60, wherein two spectrally segregated light sources 12 and 14 are used to illuminate the sample, and separate detection systems 70 and 72 are employed to detect illumination after reflection from and interaction with sample 20.

Light source 12 emits illumination over a first spectrum and light source 14 emits illumination over a second spectrum. The optical path 28 traversed by light of the first spectrum includes light source 12, beam combiner 25, optical system 32, sample 20, optical system 22, beam-splitter 31 and one, or both, of the detectors 70 and 72. The optical path 30 traversed by light of the second spectrum includes light source 14, beam combiner 25, optical system 32, sample 20, optical system 22, beam-splitter 31 and one or both, of the detectors 70 and 72.

Note that optical paths 28 and 30 are substantially coincident in the region between beam combiner 25 and beam splitter 31 and that optical system 32 is used to provide small-spot illumination of sample 20 with light originating from both of the light sources 12 and 14. Beam combiner 25 may be a prism, a beam-splitter, a dichroic mirror, or other suitable element which functions to combine a portion of the light emitted by sources 12 and 14.

Following reflection from sample 20 a portion of the reflected illumination is collected by optical system 22; the optical system is optimized over the spectral region spanning both sources 12 and 14. Optical system 22 focuses the collected illumination onto the detectors 70 and 72. Beam-splitter 31 divides the focused illumination so that each detector receives a portion of the focused illumination, and generates separate output signals in response thereto.

In FIG. 5, beam-splitter 31 is shown as a spectrally selective element. Illumination originating from light source 12 is directed along optical path 28 toward detector 70. Illumination originating from light source 14 is directed along optical 30 toward detector 72. This arrangement permits optimization of the response of each detector over a limited spectral region, thereby improving detection system performance.

One or both of detector systems 70 and 72 may be located within a $N_2$ purged environment 38 to limit the adverse effects of temperature variation, atmospheric optical absorption, etc., and improve the temporal stability of the detector response. Processor 26 records and analyzes the detector output signals.

The arrangement admits several variations. For example in one arrangement both light sources are broadband, e.g. light source 12 is a Xe lamp and light source 14 is a deuterium lamp. Here detector 72 is optimized for performance over a wavelength range spanning approximately 400–850 nm. Detector 70 is optimized for performance over a wavelength range spanning approximately 190–400 nm.

For example, in certain applications it is advantageous to employ array detectors. In this case, detector 70 is a UV enhanced photodiode or UV enhanced CCD array. Detector 72 is a photodiode or CCD array selected to provide high sensitivity and good quantum efficiency throughout the visible and NIR. In applications requiring narrow band detectors, detectors 70 and 72 are, respectively, photomultiplier tubes with photocathode materials optimized for the UV and visible-NIR regions of the spectrum. In another arrangement one or both of the sources 12 and 14 may be a laser. In this case detectors 70 and 72 may be photodiode detectors optimized at one or more laser wavelength(s).

The arrangement of FIG. 4 may be generalized to include multiple light sources and multiple optical systems. Furthermore, it may be employed in systems that include one or more optical systems used separately or in combination including reflectometers, ellipsometers, scatterometers, and optical CD metrology tools operating as single wavelength metrology systems and broadband spectroscopic instruments.

Figure 6:
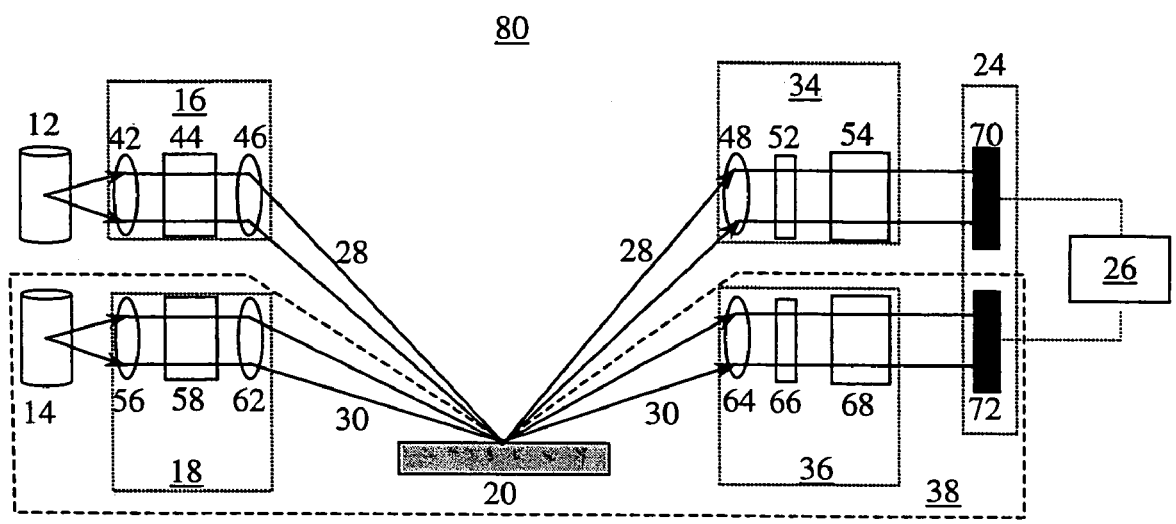
FIG. 6 is a schematic diagram of a preferred embodiment of the invention including a multiple light source ellipsometer with separate illumination sub-band optical paths and detector sub-band optical paths.

FIG. 6 illustrates a preferred embodiment of a broadband spectroscopic ellipsometry system 80. Ellipsometry system 80 includes two separate measurement systems; one optimized for VUV operation, the other for operation in the UV-NIR spectral range. Detector system 24 may include separate VUV 72 and UV-VIS 70 detectors.

The VUV ellipsometer is comprised of a VUV light source 14, optical system 18, sample 20, optics system 36 and detector 72. The VUV ellipsometer is isolated from the ambient environment and maintained in a $N_2$ purged environment 38, in order to remove optically absorbing atmospheric constituent from the optical path 30.

Optical system 18 includes condenser 56, polarizer 58, and focusing system 62 and is configured to provide small-spot illumination of the sample with polarized broadband VUV light at a measurement location. Optical system 36 includes collection optics 64, wave-plate 66 and analyzer 68 configured to collect a portion of the illumination reflected from the sample and measure the change in the illumination produced by interaction with the sample.

Detector 72 generates output signals in response to the detected illumination at a plurality of wavelengths spanning the spectral region between 140 and 190 nm. Processor 26 records and analyzes those output signals. Optical systems 18 and 36 are fabricated from VUV transparent materials and components selected from the group consisting of UV grade fused silica, $CaF_2$, $BaF_2$, $LaF_3$, LiF, $SrF_2$, $MgF_2$ and fluorine-doped fused silica. Ideally, the VUV light source 14 is a deuterium lamp with a VUV window. In the preferred embodiment polarizer 58 and analyzer 68 are VUV grade Rochon prisms and wave-plate 66 is manufactured form $MgF_2$.

The UV-NIR ellipsometer is comprised of a UV-NIR light source 12, optical system 16, sample 20, optics system 34 and detector 70. The UV-NIR ellipsometer is illustrated with optical path 28 maintained in the ambient environment; however, if so desired, this system may also be maintained in a $N_2$ purged environment in order to improve the performance of the UV-NIR measurement system.

Optical system 16 includes condenser 42, polarizer 44, and focusing system 46 and is configured to provide small-spot illumination of the sample with polarized broadband UV-NIR light at a measurement location. Optical system 34 includes collection optics 48, wave-plate 52 and analyzer 54 configured to collect a portion of the illumination reflected from the sample and measure the change in the illumination produced by interaction with the sample.

Detector 70 generates output signals in response to the detected illumination at a plurality of wavelengths spanning the spectral region between 190 and 850 nm. Processor 26 records and analyzes those output signals.

Optical systems 16 and 34 are optimized for the wavelength region spanning 190–850 nm. In the preferred embodiment, the UV-NIR light source 12 includes both deuterium and Xe lamps arranged to provide broadband illumination of the sample over the wavelength range spanning 190–850 nm. In the preferred embodiment polarizer 44 and analyzer 54 are Rochon prisms.

The VUV and UV-NIR optical systems are arranged so that the measurement regions of the VUV and UV-NIR ellipsometers are substantially identical, e.g. the size and shape of the illuminated area at the measurement location and the numerical aperture of the collection systems are virtually identical in the VUV and UV-NIR.

The arrangement of FIG. 5 may be further generalized to include additional light sources and additional measurement systems that employ gas purged optical paths. Possible generalizations include systems that use one or more measurement technologies employed separately or in combination including instruments commonly known as reflectometers, ellipsometers, scatterometers, and optical CD metrology tools operating as single wavelength metrology systems and broad-band spectroscopic instruments.

We claim:

1. An optical metrology tool for evaluating a sample comprising:
   a first light source emitting a first beam of light;
   a second light source emitting second beam of light including radiation at an ultraviolet wavelength;
   a detector for generating output signals in response to received light;
   a first optical path for directing the first light beam to the sample and for collecting the first light beam reflected from the sample and directing the collected first light beam to the detector, said first optical path being exposed to the ambient environment; and
   a second optical path for directing the second light beam to the sample and for collecting the second light beam reflected from the sample and directing the collected second light beam to the detector, said second optical path being substantially shielded from the ambient environment.

2. A metrology tool as recited in claim 1, wherein said second optical path is purged by an inert gas.

3. A metrology tool as recited in claim 2, wherein said second optical path includes beam transport tubes for shielding the second light beam from the ambient environment.

4. A metrology tool as recited in claim 1, wherein said second optical path includes optical components selected from the group consisting of UV grade fused silica, $CaF_2$, $BaF_2$, $LaF_3$, LiF, $SrF_2$, $MgF_2$ and fluorine doped fused silica.

5. A metrology tool as recited in claim 1, wherein said detector is a spectrometer.

6. A metrology tool as recited in claim 1, wherein said first light source is a xenon lamp and said second light source is a deuterium lamp.

7. A metrology tool as recited in claim 1, wherein the second light source emits light at 157 nm.

8. A metrology tool as recited in claim 1, wherein the second light source is a laser.

9. A metrology tool as recited in claim 1, wherein said detector includes first and second detector subsystems and wherein said first optical path directs the first beam of light to the first detector subsystem and wherein said second optical path directs the second beam of light to the second detector subsystem.

10. A metrology tool as recited in claim 1, which is configured as a system selected from the group consisting of spectroscopic reflectometers and spectroscopic ellipsometers.

11. A metrology tool as recited in claim 1, which is configured as a system including both a spectroscopic reflectometer and a spectroscopic ellipsometer.

12. A metrology tool as recited in claim 1, further including a processor receiving output signals from the detector for evaluating the sample.

13. A metrology tool as recited in claim 1, wherein each optical path includes an optical system configured to produce small-spot illumination on the sample at substantially the same location on the sample.

14. An optical metrology tool for evaluating a sample comprising:
   a xenon light source emitting a first beam of light;
   a deuterium light source emitting second beam of light including radiation at an ultraviolet wavelength;
   a spectrometer for generating output signals in response to received light as a function of wavelength;
   a processor receiving output signals from the spectrometer for evaluating the sample;
   a first optical path for directing the first light beam to the sample and for collecting the first light beam reflected from the sample and directing the collected first light beam to the spectrometer, said first optical path being exposed to the ambient environment;
   and a second optical path for directing the second light beam to the sample and for collecting the second light beam reflected from the sample and directing the collected second light beam to the spectrometer, said second optical path being substantially shielded from the ambient environment and purged by an inert gas.

15. A metrology tool as recited in claim 14, wherein said second optical path includes beam transport tubes for shielding the second light beam from the ambient environment.

16. A metrology tool as recited in claim 14, wherein said second optical path includes optical components selected from the group consisting of UV grade fused silica, $CaF_2$, $BaF_2$, $LaF_3$, LiF, $SrF_2$, $MgF_2$ and fluorine doped fused silica.

17. A metrology tool as recited in claim 14, wherein the deuterium light source emits light at 157 nm.

18. A metrology tool as recited in claim 14, wherein said spectrometer includes first and second detector subsystems and wherein said first optical path directs the first beam of light to the first detector subsystem and wherein said second optical path directs the second beam of light to the second detector subsystem.

19. A metrology tool as recited in claim 14, which is configured as a system selected from the group consisting of spectroscopic reflectometers and spectroscopic ellipsometers.

20. A metrology tool as recited in claim 14, which is configured as a system including both a spectroscopic reflectometer and a spectroscopic ellipsometer.

21. A metrology tool as recited in claim 14, wherein each optical path includes an optical system configured to produce small-spot illumination on the sample at substantially the same location on the sample.

* * * * *